United States Patent [19]
Kreuzer

[11] 3,987,304
[45] Oct. 19, 1976

[54] INFRARED ABSORPTION SPECTROSCOPY EMPLOYING AN OPTOACOUSTIC CELL FOR MONITORING FLOWING STREAMS

[75] Inventor: Lloyd B. Kreuzer, San Francisco, Calif.

[73] Assignee: Diax Corporation, Sunnyvale, Calif.

[22] Filed: Feb. 20, 1975

[21] Appl. No.: 551,232

[52] U.S. Cl. .................... 250/343; 356/97; 250/340
[51] Int. Cl.² .......................... G01M 21/26
[58] Field of Search ......... 250/343, 340; 181/33 A; 356/97

[56] References Cited
UNITED STATES PATENTS

| 3,560,738 | 2/1971 | Strange | 250/343 |
| 3,700,890 | 10/1972 | Kruezer | 250/343 |
| 3,727,050 | 4/1973 | Kerr | 250/343 |
| 3,787,694 | 6/1974 | Owen | 250/343 |
| 3,820,901 | 6/1974 | Kruezer | 356/97 |
| 3,881,805 | 5/1975 | Larson | 181/33 A |

Primary Examiner—Harold A. Dixon
Assistant Examiner—Bruce C. Anderson
Attorney, Agent, or Firm—Lowhurst & Aine

[57] ABSTRACT

In an infrared laser optoacoustic spectrometer, the optoacoustic cell is acoustically isolated from a flowing stream to be analyzed, such as the output stream of a retention time chromatograph, by means of mufflers disposed upstream and downstream of the optoacoustic cell.

13 Claims, 1 Drawing Figure

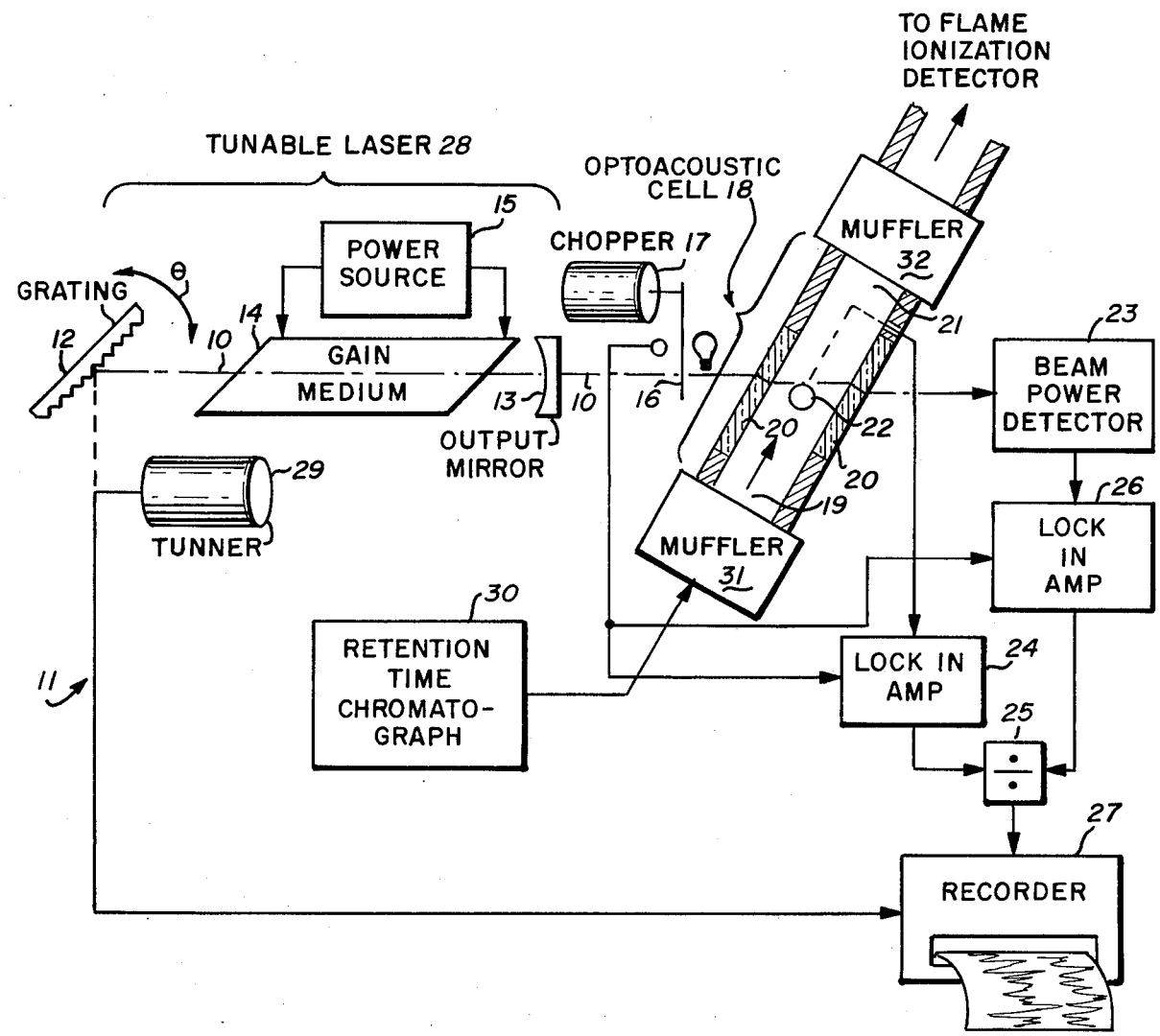

INFRARED ABSORPTION SPECTROSCOPY EMPLOYING AN OPTOACOUSTIC CELL FOR MONITORING FLOWING STREAMS

BACKGROUND OF THE INVENTION

The present invention relates in general to infrared laser absorption spectroscopy and, more particularly, to such spectroscopy wherein an optoacoustic detecting cell is arranged for monitoring a fluid stream to be analyzed.

DESCRIPTION OF THE PRIOR ART

Heretofore, infrared laser absorption spectroscopy has employed an optoacoustic sample detection cell for analyzing gaseous samples and, in particular, for detecting certain pollutants in the air to concentration levels as low as parts per billion. Such a laser spectrometer is disclosed in: U.S. Pat. No. 3,820,901 issued June 28, 1974: in an article titled "Laser Optoacoustic Spectroscopy: A New Technique of Gas Analysis" appearing in *Analytical Chemistry*, Vol. 46, No. 2 of Feb. 1974, pages 239–244: in *Science*, Vol. 177, pages 347–349 of 28 July 1972 in an article titled "Air Pollution: Sensitive Detection of Ten Pollutant Gases by Carbon Monoxide and Carbon Dioxide Lasers"; and in U.S. Pat. No. 3,659,452, issued May 2, 1972.

In these prior art laser absorption spectrometers, the laser, which is preferably a relatively high power output carbon dioxide or carbon monoxide laser, produces an output laser beam which is tunable to selected wavelengths within a band of infrared wavelengths of interest, i.e., the band of wavelengths over which certain gaseous sample constituents are known to have infrared absorption spectra. The laser output beam is directed through an optoacoustic cell containing the gaseous material to be analyzed. A sensitive microphone is coupled to the gaseous sample inside the sample cell.

The laser beam is chopped at a certain chopping frequency, as of 25 Hertz, to produce a corresponding modulation of the absorption, if any, of the laser beam energy absorbed by the sample gas under analysis. Absorption of energy from the laser beam by the gas produces heating thereof which results in generating an acoustic wave which is detected by the microphone. The detected signal is processed to produce an output signal as a function of the wavelength of the infrared energy of the tunable laser beam to derive an absorption spectrum of or absorption spectral data concerning the sample under analysis.

In these aforecited infrared laser optoacoustic spectrometers, the sample gas to be analyzed is drawn into a sample cell by means of a vacuum pump. The cell is then closed to the surrounding atmosphere by means of a valve and the absorption measurements made on the gaseous constituents of the sample.

It has also been proposed to use the aforedescribed infrared laser absorption spectrometer as a detector for a gas chromatograph. However, the output of a gas chromatograph comprises an effluent stream and while it may be possible to employ the prior art technique of drawing a sample from that stream into an optoacoustic detector cell for detection and then valving off the stream from the cell while the measurement is made, this technique would be relatively slow. It is desired to provide an improved detecting scheme wherein at least one sample is derived for each retention peak in the effluent stream of the gas chromatograph. This requires that the samples and measurements be taken and made in less than a second. Also, it is desired that the samples be obtained in such a manner as not to introduce back pressure fluctuations on the chromatographic column as this could adversely affect the timing of the retention peaks.

SUMMARY OF THE PRESENT INVENTION

The principal object of the present invention is the provision of an improved infrared absorption spectrometer employing an optoacoustic cell for monitoring flowing streams and in particular for monitoring the effluent stream of a retention time chromatograph.

In one feature of the present invention, a fluid stream to be analyzed has at least a portion thereof directed through an optoacoustic detection cell for detecting the constituents of the sample fluid and wherein acoustic isolation means are operatively associated with the optoacoustic detection cell for acoustically isolating the detection region of the cell from acoustic noises associated with the fluid stream and the surrounds of said detection cell.

In another feature of the present invention, the acoustic isolation means operatively associated with the optoacoustic detection cell comprise one or more mufflers disposed in the fluid stream flowing through the optoacoustic cell for acoustically isolating the detection region of the optoacoustic cell from acoustic noises associated with the fluid stream under analysis or acoustic noises that may tend to propagate through the fluid stream under analysis.

In another feature of the present invention, the fluid stream under analysis is the effluent stream of a retention time chromatograph.

In another feature of the present invention, the fluid under analysis is caused to continuously flow through the optoacoustic detection cell and the conditions of fluid flow through the cell are arranged to provide laminar flow therein to inhibit turbulence and generation of unwanted acoustic noises in the region of the detection cell.

Other features and advantages of the present invention will become apparent upon a perusal of the following specification taken in connection with the accompanying drawing wherein:

BRIEF DESCRIPTION OF THE DRAWING

The drawing is a schematic line diagram, partly in block diagram form, of a laser spectrometer incorporating features of the present invention.

DESCRIPTION OF THE PREFERRED EMBODIMENTS

Referring now to the drawing, there is shown an infrared laser optoacoustic spectrometer 11 incorporating features of the present invention. Briefly, the spectrometer 11 includes an optical cavity resonator defined by the optical path between a diffraction grating 12 (wavelength selector) and a partially transmissive output mirror 13. An envelope 14, having Brewster windows at opposite ends and containing a conventional laser gaseous gain medium, such as carbon monoxide, carbon dioxide, or helium-neon mixture, is interposed along the optical resonator path 10 between the grating 12 and the output mirror 13. The gain medium is excited by a suitable electrical discharge to provide coherent stimulated emission radiation at a resonant optical wavelength of the optical resonator. Power is supplied from a power source 15 to the gain medium to sustain the electrical discharge and laser action.

The output mirror is an output coupler for the laser beam and its reflectivity is preferably matched to the gain of each laser line to obtain maximum output power for each laser line (wavelength). The output laser beam is modulated by means of a rotatable perforated chopper disc 16 driven by a motor 17. An optoacoustic sample cell 18 is disposed in the modulated or chopped laser beam path. Sample gases to be analyzed are caused to flow through the sample cell 18 via inlet and outlet passageways 19 and 21. A pair of Brewster angle windows 20 are disposed in the sidewall of the cell 18 on opposite sides thereof to allow transmission of the output beam of the laser through the cell and through a sample gas in the detector region thereof.

A microphone 22 is coupled in acoustic wave energy exchanging relation with the fluid within the sample cell 18. A beam power detector 23 is disposed at the terminal end of the laser beam path for monitoring the beam power incident thereon.

In operation, each pulse of the chopped laser beam which is incident on the sample fluid within the detector cell at a wavelength corresponding to an absorption line of the sample material, produces absorption of power from the beam and consequent heating of the sample fluid within the cell 18. Heating of the gas or fluid produces expansion and generation of an acoustic wave at the chopper frequency within the sample cell 18. The acoustic waves are picked up by the microphone 22 and fed to one input of a lock-in amplifier 24 for amplification and synchronous detection against a sample of the chopper frequency, as of 10–400 Hertz, derived from the chopper 17 via a light beam directed through the chopper wheel to an optical detector 32.

The amplified and detected output signal at the output of lock-in amplifier 24 is a measure of the absorbance of the laser beam by the sample and is fed to one input of a divider 25 for division by a second signal derived from a second lock-in amplifier 26 which similarly lock-in amplifies and detects the beam power detected by the beam power detector 23. The second lock-in amplifier 26 receives a reference signal from the chopper 17 in the same manner as the reference provided for the first lock-in amplifier 24.

The output of the divider 25 corresponds to a sample absorption signal normalized to the beam power and this signal is recorded in a recorder 27 as a function of the wavelength of the tunable laser 28, as tuned by a tuner motor 29 which tunes the laser 28 by changing the angle $\theta$ of the diffraction grating 12. Thus, the recorder 27 records an absorption spectrum of the sample, such absorption spectrum being normalized to the beam power.

In case the optoacoustic sample cell region 18 is open on its ends in fluid communication with the conduit conducting the fluid stream to be analyzed, acoustic noise sources are free to couple their acoustic noise waves into the detector cell region 18 substantially reducing the signal-to-noise ratio of the detector. In the case of a retention time chromatograph 30 as the source of the effluent stream to be analyzed by the detector 18, such undesired acoustic noise sources could include turbulence in the effluent stream. Also noises could be coupled back along the stream from the exhaust region of the cell 18.

Accordingly, acoustic isolators, such as mufflers 31 and 32, are provided in the effluent stream upstream and downstream, respectively, of the detector cell region 18 for inhibiting propagation of noises through the fluid stream into the detector region 18. The acoustic isolators or mufflers 32 may comprise, for example, constrictions or baffling and are designed to provide a relatively high degree of attenuation to acoustic wave energy propagating therethrough. In a typical example the acoustic isolators 31 and 32 provide high attenuation to propagation of acoustic waves in the frequency band of the laser beam modulation and harmonics thereof superimposed on the laser beam. In a typical application, this band of acoustic noise wave energy to be attenuated most likely falls in the range of 10 to 400 Hertz. It may also be desirable to provide acoustic wave isolation and attenuation at harmonics of the laser beam modulation frequency. In some cases it may be desired to detect one or more harmonics of the beam modulation frequency, as contrasted with the fundamental.

In the optoacoustic detector cell 18 of FIG. 1 where the fluid to be analyzed flows continuously through the cell, the conditions of fluid flow through the cell are chosen to maintain laminar flow within the cell so as not to introduce unwanted noise in the cell due to the turbulence of the stream.

What is claimed is:

1. In a method of infrared absorption spectroscopy for monitoring a stream of fluid, the steps of:
    flowing a stream of fluid to be analyzed through a detection region having an infrared wave permeable window portion through which a modulated beam of infrared radiation is directed into the fluid stream to produce modulated absorption of energy from the beam by the sample fluid to generate acoustic wave energy at the modulation frequency in the detection region;
    detecting the acoustic wave energy generated in the detection region by the absorption of the beam of infrared radiation by the fluid stream; and
    muffling the fluid stream relative to the detection region to inhibit propagation of noise through the fluid stream into the detection region.

2. The method of claim 1 including, muffling the fluid stream upstream of the detection region to inhibit propagation of noise through the fluid stream into the detection region.

3. The method of claim 1 including, muffling the fluid stream upstream and downstream of the detection region to inhibit propagation of noise through the fluid stream into the detection region.

4. The method of claim 1 wherein the step of flowing the stream through the detection region includes, flowing said stream under laminar flow conditions through the detection region to inhibit turbulence within the detection region.

5. The method of claim 1 wherein the fluid stream to be analyzed is the effluent stream of a retention time chromatograph, and wherein the step of flowing the fluid stream through the detection region includes flowing at least a portion of the effluent stream of a retention time chromatograph through the detection region.

6. In an apparatus for infrared absorption spectroscopy for monitoring a stream of fluid:
    optoacoustic detector cell means having an infrared wave permeable window portion through which a modulated beam of infrared radiation is directed into a detection region of said cell means;

means for flowing a stream of fluid to be analyzed through said detection region of said detector cell means to produce modulated absorption of energy from the modulated beam via the sample fluid to generate acoustic wave energy at the modulation frequency in the detection region of said cell means;

detector means for detecting the acoustic wave energy generated in the detection region by the absorption of the beam of infrared radiation by the fluid stream; and means for muffling the fluid stream relative to the said detection region of said cell means to inhibit propagation of noise through the fluid stream into said detection region.

7. The apparatus of claim 6 wherein said muffling means includes means for muffling the fluid stream upstream of the detection region to inhibit propagation of noise through the fluid stream into said detection region.

8. The apparatus of claim 6 wherein said muffler means includes means for muffling the fluid stream upstream and downstream of said detection region to inhibit propagation of noise through the fluid stream into said detection region.

9. The apparatus of claim 6 wherein said means for flowing the stream of sample fluid through said detection region includes, means for flowing said fluid stream through said detection region in a condition of laminar flow to inhibit turbulence within said detection region.

10. The apparatus of claim 6 including, retention time chromatograph means for producing an effluent stream of fluid to be analyzed, and wherein said means for flowing a stream of fluid to be analyzed through a detection region of said cell means includes means for flowing the effluent stream of said retention time chromatograph means through the detection region of said detector cell means.

11. In an infrared absorption detecting apparatus for monitoring a stream of fluid:

conduit means for conducting a stream of fluid to be detected;

detector cell means having an infrared window through which a modulated beam of infrared energy is directed into a detection region containing sample fluid from a stream of fluid to be detected to produce modulated absorption of energy from the beam by the sample fluid to generate acoustic wave energy at the modulation frequency within said detection region, said detector cell means having inlet and outlet ports, connected in fluid communication with said conduit means for flow of fluid from said conduit means through said detector cell means;

acoustic detector means coupled in acoustic wave energy exchanging relation with the detection region of said detector cell means for detecting the acoustic wave energy generated in said detection region; and acoustic isolation means operatively associated with the fluid communication between said detector cell means and said conduit means for acoustically isolating said detection region of said detector cell from the fluid stream in said conduit means.

12. The apparatus of claim 11 wherein said acoustic isolation means includes, muffler means for muffling the fluid stream in said conduit means relative to said detection region of said detector cell means to inhibit propagation of noise through the fluid stream into said detection region.

13. The apparatus of claim 12 wherein said muffler means includes muffler means disposed in the fluid stream upstream and downstream of said detection region to inhibit propagation of noise through the fluid stream into said detection region.

* * * * *